United States Patent
Wan et al.

(10) Patent No.: US 11,857,591 B2
(45) Date of Patent: Jan. 2, 2024

(54) COMPOSITION FOR PROTECTING LIVER, PROTECTING INTESTINES AND ENHANCING IMMUNITY FOR FRESHWATER FISH, AND PREPARATION AND APPLICATION THEREOF

(71) Applicant: Freshwater Fisheries Research Institute of Jiangsu Province, Nanjing (CN)

(72) Inventors: Jinjuan Wan, Nanjing (CN); Hui Xue, Nanjing (CN); Sheng Yuan, Nanjing (CN); Aijun Xia, Nanjing (CN); Yanhua Zhao, Nanjing (CN); Meifang Shen, Nanjing (CN)

(*) Notice: Subject to any disclaimer, the term of this patent is extended or adjusted under 35 U.S.C. 154(b) by 0 days.

(21) Appl. No.: 17/213,419

(22) Filed: Mar. 26, 2021

(65) Prior Publication Data
US 2022/0347249 A1 Nov. 3, 2022

Related U.S. Application Data

(63) Continuation of application No. PCT/CN2020/126004, filed on Nov. 3, 2020.

(30) Foreign Application Priority Data
Apr. 10, 2020 (CN) .................. 202010279423.7

(51) Int. Cl.
| | |
|---|---|
| A23K 10/30 | (2016.01) |
| A61K 31/145 | (2006.01) |
| A61K 33/00 | (2006.01) |
| A61K 36/22 | (2006.01) |
| A61K 36/315 | (2006.01) |
| A61K 36/704 | (2006.01) |
| A61K 36/708 | (2006.01) |
| A61P 37/04 | (2006.01) |
| A61K 36/19 | (2006.01) |
| A23K 50/80 | (2016.01) |

(52) U.S. Cl.
CPC .............. *A61K 36/19* (2013.01); *A23K 10/30* (2016.05); *A23K 50/80* (2016.05); *A61K 31/145* (2013.01); *A61K 33/00* (2013.01); *A61K 36/22* (2013.01); *A61K 36/315* (2013.01); *A61K 36/704* (2013.01); *A61K 36/708* (2013.01); *A61P 37/04* (2018.01)

(58) Field of Classification Search
None
See application file for complete search history.

(56) References Cited

FOREIGN PATENT DOCUMENTS

| | | | |
|---|---|---|---|
| CN | 107373189 A | * | 11/2017 |
| CN | 109588372 A | * | 4/2019 |
| KR | 2017058215 A | * | 5/2017 |

OTHER PUBLICATIONS

Machine translation of CN-107373189-A.*
Machine translation of CN-109588372-A.*
Machine translation of KR-2017058215-A.*

* cited by examiner

*Primary Examiner* — H. Sarah Park

(57) ABSTRACT

A composition for protecting liver, protecting intestines and enhancing immunity for freshwater fish is disclosed, including the following raw materials in parts by weight: 15~27 parts of *Andrographis herba*, 18~22 parts of *Isatidis folium*, 10~15 parts of *Polygonum hydropiper*, 8~12 parts of *Rheum palmatum* L., and 8~12 parts of *Galla chinensis*. And the preparation and the application of the composition are disclosed. The composition of the disclosure has the effect of resisting bacteria, scavenge free radicals, clearing heat, detoxifying, preventing and treating enteritis and the like, which can effectively improve the immunity of the freshwater fish and ensure the health of the organism.

2 Claims, 2 Drawing Sheets

COMPOSITION FOR PROTECTING LIVER, PROTECTING INTESTINES AND ENHANCING IMMUNITY FOR FRESHWATER FISH, AND PREPARATION AND APPLICATION THEREOF

CROSS-REFERENCE TO RELATED APPLICATIONS

This application is a continuation of International Patent Application No. PCT/CN2020/126004 with a filing date of Nov. 3, 2020, designating the United States, now pending, and further claims priority to Chinese Patent Application No. 202010279423.7 with a filing date of Apr. 10, 2020. The content of the aforementioned applications, including any intervening amendments thereto, are incorporated herein by reference.

TECHNICAL FIELD

The present disclosure relates to the field of aquaculture technology, and more specifically, to a composition for protecting liver, protecting intestines and enhancing immunity for freshwater fish, and a preparation and an application thereof.

BACKGROUND

In recent years, with the rapid development of intensive farming, a series of problems and difficulties have arisen in aquaculture, especially in freshwater fish. On the one hand, the problem of fish diseases caused by intensive farming is becoming increasingly prominent, and the aquaculture water environment is also deteriorating. On the other hand, in the harsh environment, the metabolism of fish is becoming increasingly disordered and the immunity is declining, and the non-standard use and abuse of drugs further damage the ecological balance of the water area.

Traditionally, the treatment and prevention of freshwater fish diseases mainly rely on antibiotics, chemicals and so on. However, the abuse of these drugs is easy to cause environmental pollution, drug residues, drug resistance of pathogenic microorganisms, immunosuppression and destruction of the body's microecological balance and many other negative effects, which seriously plagues the freshwater fish breeding industry. Therefore, how to improve the immunity and physiological function of fish and reduce breeding diseases is an urgent problem for those skilled in the art.

SUMMARY

In view of the above, an object of the present disclosure is to provide a composition for protecting liver, protecting intestines and enhancing immunity for freshwater fish, which can effectively improve the immunity of freshwater fish and ensure the health of the body.

Technical solutions of the present disclosure are specifically described as follows.

A composition for protecting liver, protecting intestines and enhancing immunity for freshwater fish includes following raw materials in parts by weight:
  15~27 parts of *Andrographis herba*;
  18~22 parts of *Isatidis folium*;
  10~15 parts of *Polygonum hydropiper*;
  8~12 parts of *Rheum palmatum* L.; and
  8~12 parts of *Galla chinensis*.

The disclosure aims at the physiological metabolism mechanism of freshwater fish. And based on its immune mechanism, *Andrographis herba*, *Isatidis folium*, *Polygonum hydropiper*, *Rheum palmatum* L. and *Galla chinensis* are selected from Chinese herbal medicine, which have the following effects.

1. *Andrographis herba*, *Isatidis folium*, *Rheum palmatum* L. are related to each other to enhance the efficacy.

2. *Andrographis herba*, *Isatidis folium*, *Rheum palmatum* L. and *Galla chinensis* are all cold, while *Polygonum hydropiper* is slightly cold. They all have the effect of clearing away heat and detoxification. The combination of them can improve the body's antibacterial and disease resistance.

3. *Galla chinensis* contains tannic acid, which can cause steatosis of liver cells and aggravate its toxicity. *Andrographis herba* and *Isatidis folium* can prevent liver injury, *Polygonum hydropiper* can help liver eliminate toxins, and *Rheum palmatum* L. can inhibit liver lipid peroxidation. Therefore, their compatibility can relieve the liver injury caused by *Galla chinensis*.

4. *Andrographis herba* can regulate gastrointestinal system. *Isatidis folium* has a good protective effect on the balance of intestinal microbial ecosystem. *Rheum palmatum* L. can protect intestinal mucosal barrier, prevent intestinal bacterial translocation, remove intestinal bacteria and toxins, and promote intestinal movement and metabolism. *Galla chinensis* and *Polygonum hydropiper* are effective in the treatment of intestinal inflammation. Five kinds of medicines are compounded to maintain the intestinal health in an all-round way.

Preferably, the above composition further includes following raw materials in parts by weight:
  7~10 parts of taurine; and/or
  15~20 parts of diatomite.

Generally, the commercial feed of freshwater fish is relatively cheap, and its fish meal content is low. On the one hand, taurine can provide the necessary amino acids for fish, improve the body's antioxidant function and immunity, and has a significant protective effect on liver; on the other hand, taurine combined with the above Chinese herbal medicine can more effectively inhibit liver fibrosis.

Diatomite has neutral pH value, non-toxic, unique pore structure, light weight, large porosity and strong adsorption performance. On the one hand, the addition of the diatomite is conducive to the uniform dispersion of the components in the composition, and at the same time, it is not easy to separate and precipitate. On the other hand, it can improve digestion and metabolism, promote nutrient absorption, save raw materials and improve feed utilization. It can also be used as antiseptic. At the same time, diatomite can supplement minerals, enhance animal immune system function, strengthen disease resistance.

The compound of the seven components in the disclosure can not only overcome the shortcomings of a single drug, but also enhance the curative effect, which can be described as "learning from each other, complementing each other". It can directly improve the disease resistance ability of the fish body, remove the free radicals in the fish body, eliminate the negative effects of free radicals on the normal functions of the body tissues and organs, accelerate the repair of the damaged immune system, and improve the digestion and absorption energy of the intestinal tract power. It can promote the growth of fish, and improve the survival rate.

A preparation method for the above composition for protecting liver, protecting intestines and enhancing immunity for freshwater fish includes:

crushing each of the raw materials coarsely, sieving each of the crushed raw materials with a sieve of 80 mesh, pulverizing each of the sieved raw materials by an ultra-micro crusher with wall breaking at a low temperature, sieving each of the pulverized raw materials with a sieve of 300 mesh, and mixing all the raw materials well.

Preferably, the pulverizing temperature of low-temperature wall breaking is −10~−25° C.

An application of the above composition for protecting liver, protecting intestines and enhancing immunity for freshwater fish in preparation of a preparation for resisting bacteria and/or improving immunity and/or protecting liver and intestines is provided.

An application of the above composition for protecting liver, protecting intestines and enhancing immunity for freshwater fish in preparation of a functional feed is provided.

Preferably, based on weight percentage, the adding amount of the above composition for protecting liver, protecting intestines and enhancing immunity for freshwater fish in the functional feed is 0.4-0.7%.

In the technical scheme, the composition has the effect of resisting bacteria, scavenge free radicals, clearing heat, detoxifying, preventing and treating enteritis and the like, which can effectively improve the immunity of the freshwater fish and ensure the health of the organism.

DETAILED DESCRIPTION OF EMBODIMENTS

Figure 1:
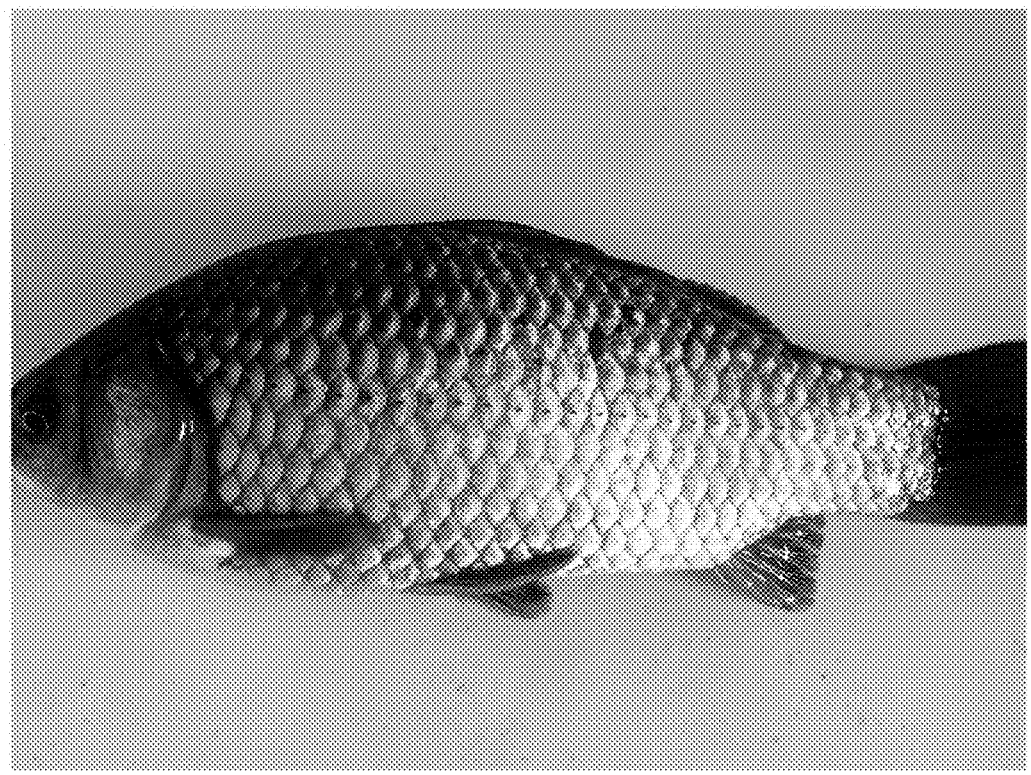
FIG. 1 shows the surviving crucian carp after challenge (using the compound Chinese herbal medicine composition for protecting liver, protecting intestines and enhancing immunity)

Technical solutions of the present disclosure will be clearly and completely described below with reference to the embodiments. Obviously, the described embodiments are only part of the embodiments of the present disclosure, not all of them. Other embodiments made by those skilled in the art without sparing any creative effort should fall within the scope of the disclosure.

Embodiment 1

20 parts by weight of *Andrographis herba,* 20 parts by weight of *Isatidis folium,* 10 parts by weight of *Polygonum hydropiper,* 10 parts by weight of *Rheum palmatum* L., 10 parts by weight of *Galla chinensis,* 10 parts by weight of taurine, and 20 parts by weight of diatomite were weighed. Each of the raw materials was crushed coarsely. Each of the crushed raw materials was pulverized by an ultra-micro crusher with wall breaking at −20° C. Each of the pulverized raw materials was sieved with a sieve of 300 mesh, and all the raw materials were mixed well to obtain a compound Chinese herbal medicine composition for protecting liver, protecting intestines and enhancing immunity.

Embodiment 2

Freshwater fish mainly rely on their non-specific immune system to protect themselves. The levels of lysozyme, immunoglobulin M, superoxide dismutase, malondialdehyde and total antioxidant capacity are directly related to the immune status of the body. The activities of aspartate aminotransferase and alanine aminotransferase can reflect the health status of liver. Intestinal health can be tested by the activities of digestive enzymes such as trypsin, lipase and amylase. Therefore, the embodiment evaluated the immunity and organism health of the crucian carp through the above indicators.

Growth test: nine crucian carp ponds (identical in size, density of crucian carp stocking, and mode of management) were randomly selected and divided into groups in Huangshagang area of Sheyang County, Jiangsu Province, China.

Control group A (fed with a basic commercial feed);

Control group B (supplemented with 0.5% *Andrographis herba* in the basic commercial feed);

Control group C (supplemented with 0.5% *Isatidis folium* in the basic commercial feed);

Control group D (supplemented with 0.5% *Polygonum hydropiper* in the basic commercial feed);

Control group E (supplemented with 0.5% *Rheum palmatum* L. in the basic commercial feed);

Control group F (supplemented with 0.5% *Galla chinensis* in the basic commercial feed);

Control group G (supplemented with 0.15% *Andrographis herba,* 0.1% *Isatidis folium,* 0.05% *Polygonum hydropiper,* 0.05% *Rheum palmatum* L., 0.05% *Galla chinensis* and 0.1% diatomite in the basic commercial feed);

Control group H (supplemented 0.15% *Andrographis herba,* 0.1% *Isatidis folium,* 0.05% *Polygonum hydropiper,* 0.05% *Rheum palmatum* L., 0.05% *Galla chinensis* and 0.1% taurine in the basic commercial feed);

Test group (supplemented with 0.5% of the compound Chinese herbal medicine composition for protecting liver, protecting intestines and enhancing immunity prepared in embodiment 1 in the basic commercial feed).

Each group was fed once a day in the morning, middle and evening (07:00, 12:00, 19:00). Each group was fed continuously for 10 days/month, and the rest of the time was fed with the basic commercial feed. After 4 months of domestication, the samples were collected and the indexes were tested in late July (10 fish were randomly taken from each pond). The activities of lysozyme (LZM), immunoglobulin M (IgM), alanine aminotransferase (ALT) and aspartate aminotransferase (AST) in serum, superoxide dismutase (SOD), malondialdehyde (MDA) and total antioxidant capacity (T-AOC) in liver, and trypsin (TPS), lipase (LPS) and amylase (AMS) in intestine were detected. The test results are shown in Table 1.

TABLE 1

| Index | Control group A | Control group B | Control group C | Control group D | Control group E | Control group F | Control group G | Control group H | Test group |
|---|---|---|---|---|---|---|---|---|---|
| LZM (U/ml) | 11.94 | 18.16 | 14.17 | 16.11 | 14.03 | 15.07 | 22.22 | 27.78 | 33.33 |
| IgM (mg/ml) | 1.32 | 1.49 | 1.42 | 1.46 | 1.51 | 1.41 | 1.91 | 2.10 | 2.32 |
| ALT (U/L) | 4.87 | 4.32 | 4.41 | 4.5 | 4.46 | 4.62 | 3.14 | 3.16 | 2.83 |
| AST (U/L) | 27.62 | 20.76 | 23.74 | 22.8 | 23.88 | 23.5 | 19.39 | 20.62 | 18.02 |
| SOD (U/mgprot) | 904.5 | 967.15 | 961.15 | 948.58 | 945.06 | 932.96 | 957.16 | 977.23 | 1058.29 |
| MDA (nmol/mgprot) | 21.71 | 14.27 | 14.17 | 12.69 | 16.52 | 16.17 | 12.72 | 13.25 | 11.09 |
| T-AOC (mmol/gprot) | 0.1 | 0.15 | 0.15 | 0.14 | 0.15 | 0.13 | 0.16 | 0.18 | 0.19 |
| TPS (U/mgprot) | 30017.43 | 34885.14 | 36154.93 | 38673.52 | 35504.68 | 35221.45 | 47104.29 | 45049.62 | 49158.97 |
| LPS (U/mgprot) | 1.63 | 1.92 | 2.06 | 2.16 | 1.89 | 2.22 | 2.55 | 2.64 | 3.10 |
| AMS (U/mgprot) | 72.71 | 86.14 | 86.81 | 89.51 | 86.32 | 89.51 | 91.15 | 95.5 | 108.77 |

The results showed that: compared with the control groups A-H, the levels of lysozyme (LZM) in serum in the test group were increased by 179.15%, 83.54%, 135.22%, 106.89%, 137.56%, 121.17%, 50.00% and 19.98%, respectively; the content of immunoglobulin M (IgM) in serum in the test group increased by 75.76%, 55.70%, 63.38%, 58.90%, 53.64%, 64.54%, 21.47% and 10.48% respectively; the activity of alanine aminotransferase (ALT) in serum in the test group decreased by 41.89%, 34.49%, 35.83%, 37.11%, 36.55%, 38.74%, 9.87% and 10.44%, respectively; the activity of aspartate aminotransferase (AST) in the test group decreased by 34.76%, 13.20%, 24.09%, 20.96%, 24.54%, 23.32%, 7.07% and 12.61%, respectively; the activity of superoxide dismutase (SOD) in the liver of fish in the test group increased by 17.00%, 9.42%, 10.11%, 10.57%, 11.98%, 13.43%, 10.57% and 8.29%, respectively; the content of malondialdehyde (MDA) in the test group decreased by 48.92%, 22.28%, 22.28%, 12.81%, 32.87%, 31.42%, 12.81% and 16.30%, respectively; the total antioxidant capacity (T-AOC) in the liver of fish in the test group increased by 90.00%, 26.67%, 26.67%, 35.71%, 26.67%, 46.15%, 18.75% and 5.56%, respectively; the activity of intestinal trypsin (TPS) in the test group increased by 63.77%, 40.92%, 35.97%, 27.11%, 38.46%, 39.57%, 4.36% and 9.12%, respectively; the activity of intestinal lipase (LPS) in the test group increased by 90.18%, 61.46%, 50.49%, 43.52%, 64.02%, 39.64%, 21.57% and 17.42%, respectively; the activity of intestinal amylase (AMS) in the test group increased by 49.59%, 26.27%, 25.30%, 21.52%, 26.01%, 21.52%, 19.33% and 13.90%, respectively. Therefore, compared with the control groups, the compound Chinese herbal medicine composition for protecting liver, protecting intestines and enhancing immunity with seven components can improve the immunity and antioxidant capacity of freshwater fish, and promote the health of liver and intestine.

Embodiment 3

Challenge test: after the 4-month growth test in embodiment 2, all groups of crucian carp were fasted for 24 hours, and the crucian carp with the same specifications were selected from each pond for Aeromonas hydrophila infection test.

The challenge test was carried out in a plastic box (1.0 m×0.4 m×0.4 m), with three replicates in each group and 30 fish in each replicate. Aeromonas hydrophila was provided by the fish disease laboratory of Jiangsu Freshwater Fisheries Research Institute. The final concentration of Aeromonas hydrophila was about $5 \times 10^7$ cells/ml diluted with sterile normal saline. The physiological activities of fish were observed after intraperitoneal injection of 1.0 ml bacterial solution per 100 g fish. The cumulative mortality of nine groups of fish at 0 h, 12 h, 24 h, 48 h and 96 h after challenge was counted, respectively. The results are shown in Table 2.

TABLE 2

| Group | \multicolumn{5}{c}{Cumulative mortality (%)} |
|---|---|---|---|---|---|
|  | 0 h | 12 h | 24 h | 48 h | 96 h |
| Control group A | 0.00 | 10.00 | 21.11 | 41.11 | 61.11 |
| Control group B | 0.00 | 3.33 | 6.67 | 17.78 | 38.89 |
| Control group C | 0.00 | 6.67 | 10.00 | 23.33 | 48.89 |
| Control group D | 0.00 | 3.33 | 7.78 | 17.78 | 44.44 |
| Control group E | 0.00 | 5.56 | 13.33 | 22.22 | 46.67 |
| Control group F | 0.00 | 4.44 | 12.22 | 18.89 | 45.56 |
| Control group G | 0.00 | 2.22 | 5.56 | 14.44 | 31.11 |
| Control group H | 0.00 | 2.22 | 3.33 | 13.33 | 27.78 |
| Test Group | 0.00 | 1.11 | 2.22 | 7.78 | 18.89 |

Figure 2:
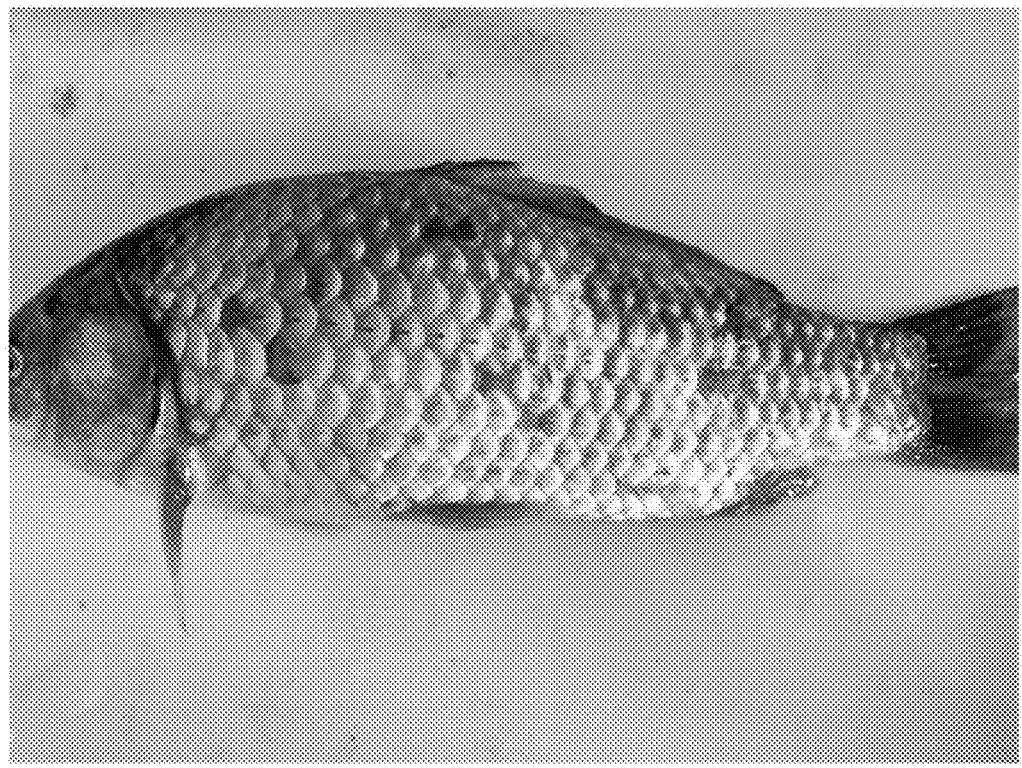
FIG. 2 shows the dead crucian carp after challenge (without using the compound Chinese herbal medicine composition for protecting liver, protecting intestines and enhancing immunity)
Figure 3:
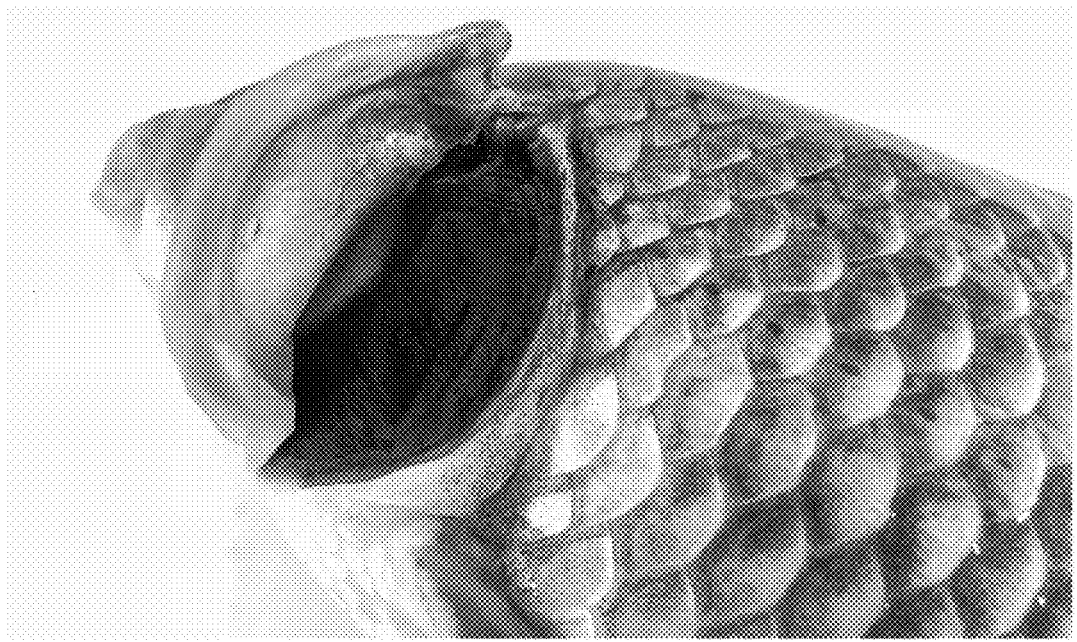
FIG. 3 shows the gill of the dead crucian carp after challenge.
Figure 4:
FIG. 4 shows the abdomen of the dead crucian carp after challenge.

The results showed that after the crucian carp was infected with Aeromonas hydrophila, the viability began to decrease, and the abdomen and gills of the dead crucian carp had bleeding symptoms in various degrees (the comparison of symptoms is shown in FIG. 1-4). Compared to the control groups A-H, the mortality of test fish 12 h after challenge was reduced by 88.90%, 66.70%, 83.35%, 66.70%, 80.02%, 75.03%, 50.05% and 50.05%, respectively; the mortality of test fish 24 h after challenge was reduced by 89.48%, 66.70%, 77.80%, 71.46%, 83.35%, 81.84%, 60.04% and 33.40%, respectively; the mortality of test fish 48 h after challenge was reduced by 81.08%, 56.24%, 6%, 6.66%, 56.24%, 64.99%, 58.81%, 46.14% and 41.65%, respectively; the mortality of test fish 96 h after challenge was reduced by 69.09%, 51.43%, 61.36%, 57.50%, 59.52%, 58.53%, 39.28% and 22.00%, respectively. Therefore, the compound Chinese herbal medicine composition for protecting liver, protecting intestines and enhancing immunity with seven components can improve freshwater fish's ability to resist *Aeromonas hydrophila* infection and reduce death caused by pathogenic bacteria.

Embodiment 4

15 parts by weight of *Andrographis herba*, 18 parts by weight of *Isatidis folium*, 15 parts by weight of *Polygonum hydropiper*, 12 parts by weight of *Rheum palmatum* L., 12 parts by weight of *Galla chinensis*, 10 parts by weight of taurine, and 18 parts by weight of diatomite were weighed. Each of the raw materials was crushed coarsely. Each of the crushed raw materials was pulverized by an ultra-micro crusher with wall breaking at −20° C. Each of the pulverized raw materials was sieved with a sieve of 300 mesh, and all the raw materials were mixed well to obtain a compound Chinese herbal medicine composition for protecting liver, protecting intestines and enhancing immunity.

Embodiment 5

25 parts by weight of *Andrographis herba*, 20 parts by weight of *Isatidis folium*, 10 parts by weight of *Polygonum hydropiper*, 8 parts by weight of *Rheum palmatum* L., 10 parts by weight of *Galla chinensis*, 8 parts by weight of taurine, and 19 parts by weight of diatomite were weighed. Each of the raw materials was crushed coarsely. Each of the crushed raw materials was pulverized by an ultra-micro crusher with wall breaking at −20° C. Each of the pulverized raw materials was sieved with a sieve of 300 mesh, and all the raw materials were mixed well to obtain a compound Chinese herbal medicine composition for protecting liver, protecting intestines and enhancing immunity.

Embodiment 6

23 parts by weight of *Andrographis herba*, 22 parts by weight of *Isatidis folium*, 14 parts by weight of *Polygonum hydropiper*, 9 parts by weight of *Rheum palmatum* L., 8 parts by weight of *Galla chinensis*, 9 parts by weight of taurine, and 15 parts by weight of diatomite were weighed. Each of the raw materials was crushed coarsely. Each of the crushed raw materials was pulverized by an ultra-micro crusher with wall breaking at −20° C. Each of the pulverized raw materials was sieved with a sieve of 300 mesh, and all the raw materials were mixed well to obtain a compound Chinese herbal medicine composition for protecting liver, protecting intestines and enhancing immunity.

Embodiment 7

21 parts by weight of *Andrographis herba*, 21 parts by weight of *Isatidis folium*, 12 parts by weight of *Polygonum hydropiper*, 11 parts by weight of *Rheum palmatum* L., 11 parts by weight of *Galla chinensis*, 7 parts by weight of taurine, and 17 parts by weight of diatomite were weighed. Each of the raw materials was crushed coarsely. Each of the crushed raw materials was pulverized by an ultra-micro crusher with wall breaking at −15° C. Each of the pulverized raw materials was sieved with a sieve of 300 mesh, and all the raw materials were mixed well to obtain a compound Chinese herbal medicine composition for protecting liver, protecting intestines and enhancing immunity.

Embodiment 8

19 parts by weight of *Andrographis herba*, 19 parts by weight of *Isatidis folium*, 13 parts by weight of *Polygonum hydropiper*, 12 parts by weight of *Rheum palmatum* L., 12 parts by weight of *Galla chinensis*, 9 parts by weight of taurine, and 16 parts by weight of diatomite were weighed. Each of the raw materials was crushed coarsely. Each of the crushed raw materials was pulverized by an ultra-micro crusher with wall breaking at −15° C. Each of the pulverized raw materials was sieved with a sieve of 300 mesh, and all the raw materials were mixed well to obtain a compound Chinese herbal medicine composition for protecting liver, protecting intestines and enhancing immunity.

Embodiment 9

Following the method of the growth test in embodiment 2 and the challenge test in embodiment 3, the physiological and biochemical indexes and the cumulative mortality (only 24 h and 48 h after challenge) of crucian carp fed with the compound Chinese herbal medicine composition for protecting liver, protecting intestines and enhancing immunity prepared in embodiments 4-9 were determined, respectively. The control group was fed with the basic commercial feed, and each test group was fed with the basic commercial feed added with 0.5% of the compound Chinese herbal medicine composition for protecting liver, protecting intestines and enhancing immunity prepared in embodiments 4-9, respectively (test group A, test group B, test group C, test group D, and test group E, respectively). The results are presented in Tables 3 and Tables 4.

TABLES 3

| Index | Group | | | | | |
|---|---|---|---|---|---|---|
| | Control group | Test group A | Test group B | Test group C | Test group D | Test group E |
| LZM (U/ml) | 11.94 | 29.17 | 37.55 | 36.21 | 32.76 | 30.55 |
| IgM (mg/ml) | 1.32 | 2.25 | 2.75 | 2.54 | 2.16 | 2.37 |
| ALT (U/L) | 4.87 | 2.85 | 2.56 | 2.74 | 2.95 | 2.93 |
| AST (U/L) | 27.62 | 20.10 | 19.47 | 20.02 | 19.25 | 19.72 |
| SOD (U/mgprot) | 904.50 | 992.48 | 1104.78 | 1099.45 | 988.45 | 1033.51 |

TABLES 3-continued

| Index | Control group | Test group A | Test group B | Test group C | Test group D | Test group E |
|---|---|---|---|---|---|---|
| MDA (nmol/mgprot) | 21.71 | 13.46 | 10.95 | 12.44 | 12.60 | 13.68 |
| T-AOC (nmol/gprot) | 0.10 | 0.18 | 0.19 | 0.19 | 0.18 | 0.17 |
| TPS (U/mgprot) | 30017.43 | 49186.06 | 48457.12 | 49020.45 | 49798.34 | 50280.21 |
| LPS (U/mgprot) | 1.63 | 3.05 | 2.84 | 2.78 | 2.94 | 3.35 |
| AMS (U/mgprot) | 72.71 | 107.51 | 100.24 | 98.24 | 100.84 | 109.39 |

TABLES 4

| Group | Cumulative mortality (%) | |
|---|---|---|
| | 24 h | 48 h |
| Control group | 21.11 | 41.11 |
| Test group A | 6.67 | 8.89 |
| Test group B | 3.33 | 5.56 |
| Test group C | 5.56 | 7.78 |
| Test group D | 6.67 | 8.89 |
| Test group E | 5.56 | 7.78 |

The general principle as defined herein may be achieved in other embodiments without departing from the spirit or scope of the disclosure. The present disclosure will therefore not be restricted to these embodiments shown herein, but rather to comply with the broadest scope consistent with the principles and novel features disclosed herein.

What is claimed is:

1. A composition for protecting liver, protecting intestines and enhancing immunity for freshwater fish, comprising the following materials in parts by weight:
   15-27 parts of *Andrographis herba;*
   18-22 parts of *Isatidis folium;*
   10-15 parts of *Polygonum hydropiper;*
   8-12 parts of *Rheum palmatum* L.;
   8-12 parts of *Galla chinensis;*
   7-10 parts of *taurine;* and
   15-20 parts of *diatomite.*

2. A method for preparing a composition, comprising:
   crushing each of the raw materials,
   sieving the crushed raw materials with a sieve of 80 mesh,
   pulverizing the sieved raw materials by a crusher at a temperature between −10° C. and −25° C.,
   sieving the pulverized raw materials with a sieve of 300 mesh, and
   mixing the sieved raw materials;
   wherein the raw materials comprises:
   15-27 parts of *Andrographis herba;*
   18-22 parts of *Isatidis folium;*
   10-15 parts of *Polygonum hydropiper;*
   8-12 parts of *Rheum palmatum* L.;
   8-12 parts of *Galla chinensis;*
   7-10 parts of *taurine;* and
   15-20 parts of *diatomite.*

* * * * *